US008349807B2

(12) United States Patent
Chiba et al.

(10) Patent No.: US 8,349,807 B2
(45) Date of Patent: Jan. 8, 2013

(54) METHOD OF IMMUNIZING ANIMAL, COMPOSITION FOR IMMUNIZATION, METHOD FOR PRODUCING ANTIBODY, METHOD FOR PRODUCING HYBRIDOMA AND METHOD FOR PRODUCING MONOCLONAL ANTIBODY

(75) Inventors: Joe Chiba, Yokohama (JP); Jun-ichi Hata, Gotenba (JP); Naoki Nishiguchi, Mishima-gun (JP); Masahiro Furutani, Takatsuki (JP)

(73) Assignees: Joe Chiba, Kanagawa (JP); Sekisui Chemical Co., Ltd., Osaka (JP)

( * ) Notice: Subject to any disclaimer, the term of this patent is extended or adjusted under 35 U.S.C. 154(b) by 1043 days.

(21) Appl. No.: 11/665,270

(22) PCT Filed: Oct. 14, 2005

(86) PCT No.: PCT/JP2005/018953
§ 371 (c)(1),
(2), (4) Date: May 5, 2008

(87) PCT Pub. No.: WO2006/041157
PCT Pub. Date: Apr. 20, 2006

(65) Prior Publication Data
US 2009/0041761 A1 Feb. 12, 2009

(30) Foreign Application Priority Data
Oct. 15, 2004 (JP) .................................. 2004-301887

(51) Int. Cl.
A61K 48/00 (2006.01)
C12N 5/04 (2006.01)
C12N 15/06 (2006.01)
(52) U.S. Cl. ........................ 514/44 R; 435/374; 435/449
(58) Field of Classification Search .......................... None
See application file for complete search history.

(56) References Cited

U.S. PATENT DOCUMENTS

| 6,482,614 B1 | 11/2002 | Young |
| 2004/0146969 A1 | 7/2004 | Furutani et al. |
| 2005/0260710 A1 | 11/2005 | Suzuki et al. |
| 2007/0026501 A1 | 2/2007 | Izumoto et al. |
| 2007/0059794 A1 | 3/2007 | Ideno et al. |
| 2007/0092937 A1 | 4/2007 | Togi et al. |

FOREIGN PATENT DOCUMENTS

| JP | 2001-33449 | | 2/2001 |
| JP | 2002-119286 | | 4/2002 |
| JP | 2004-24095 | | 1/2004 |
| JP | 2004-43447 | | 2/2004 |
| JP | 2004-81199 | | 3/2004 |
| WO | 94/29459 | | 12/1994 |
| WO | 00/66756 | | 11/2000 |
| WO | 00/75346 | A1 | 12/2000 |
| WO | 01/29233 | | 4/2001 |
| WO | 02/12281 | A2 | 2/2002 |
| WO | 02/052029 | A1 | 7/2002 |
| WO | 2004/035769 | | 4/2004 |
| WO | 2004/092221 | A1 | 10/2004 |
| WO | 2004/096859 | A1 | 11/2004 |
| WO | 2004/096860 | A1 | 11/2004 |

OTHER PUBLICATIONS

MeshTerm information downloaded from NLM on Apr. 26, 2010.*
Anthony et al (Vaccine, 1999, vol. 17, pp. 373-383.*
Yokoyama, ('Production of monoclonal antibodies' In: Current Protocols in Immunology, 1991, pp. 2.5.1-2.5.17).*
Nishihara et al., "Chaperone Coexpression Plasmids: Differential and Synergistic Roles of DnaK-DnaJ-GrpE and GroEL-GroEs in Assisting Folding of an Allergen of Japanese Cedar Pollen, Cryj2, in *Escherichia coli*", *Applied and Environmental Microbiology*, May 1998, vol. 64, No. 5, pp. 1694-1699.
Dueñas et al., "Intra- and Extracellular Expression of an scFv Antibody Fragment in *E. coli*: Effect of Bacterial Strains and Pathway Engineering Using GroES/L Chaperonins", *BoTechniques*, 1994, vol. 16, No. 3, pp. 476-477, 480-483.
Mavrangelos et al., "Increased Yield and Activity of Soluble Single-Chain Antibody Fragments by Combining High-Level Expression and the Skp Periplasmic Chaperonin", *Protein Expression and Purification*, 2001, vol. 23. pp. 289-295.
Söderlind et al., "Chaperonin Assisted Phage Display of Antibody Fragments on Filamentous Bacteriophages", *Bio/Technology*, Apr. 1993, vol. 11, pp. 503-507.
Gupta R., "Evolution of the Chaperonin Families (Hsp60, Hsp10 and Tcp-1) of Proteins and the Origin of Eukaryotic Cells", *Molecular Microbiology*, 1995, vol. 15, No. 1, pp. 1-11.
Trent et al., "Chaperonin Filaments: The Archaeal Cytoskeleton?", *Proc. Natl. Acad. Sci. USA*, May 1997, vol. 94, pp. 5383-5388.
Kubota et al., "The chaperonin containing t-complex polypeptide 1 (TCP-1) Multisubunit machinery assisting in protein folding and assembly in the eukaryotic cytosol", *Eur. J. Biochem.*, 1995, vol. 230, pp. 3-16.
Furutani et al., "Group II Chaperonin in a Thermophilic Methanogen, *Methanococcus thermolithotrophicus*", *The Journal of Biological Chemistry*, Oct. 1998, vol. 273, No. 43, pp. 28399-28407.
Gobert et al., "*Helicobacter pylori* Heat Shock Protein 60 Mediates Interleukin-6 Production by Macrophages via a Toll-like Receptor (TLR)-2-, TLR-4-, and Myeloid Differentiation Factor 88-independent Mechanism", *The Journal of Biological Chemistry*, Jan. 2004, vol. 279, No. 1, pp. 245-250.

(Continued)

*Primary Examiner* — Karen Canella
(74) *Attorney, Agent, or Firm* — Wenderoth, Lind & Ponack, L.L.P.

(57) ABSTRACT

It is an object of the present invention to a method whereby a humoral immune response is induced more efficiently in producing an antibody against an antigen protein by gene immunization. A fusion gene composed of a gene encoding the full-length of a part of the antigen protein or a gene encoding a chaperonin subunit or a chaperonin subunit linkage linked thereto is administered to express the fusion gene in the animal, thereby inducing a humoral immune response to an antigen protein by administering. An example of the chaperonin includes *Escherichia coli* GroEL. There is also provided with a composition for immunization, a method for producing an antibody, a method for producing a hybridoma, and a method for producing a monoclonal antibody.

28 Claims, 3 Drawing Sheets

OTHER PUBLICATIONS

M. Pavlenko et al., "Comparison of PSA-Specific CD8+ CTL Responses and Antitumor Immunity Generated by Plasmid DNA Vaccines Encoding PSA-HSP Chimeric Proteins", Cancer Immunology Immunotherapy, vol. 53, No. 12, pp. 1085-1092, Jun. 4, 2004.

C. Barrios et al., "Heat Shock Proteins as Carrier Molecules: in vivo Helper Effect Mediated by *Escherichia coli* GroEL and DnaK Proteins Requires Cross-Linking with Antigen", Clinical and Experimental Immunology, vol. 98, No. 2, pp. 229-233, Nov. 1994.

D. B. Lowrie et al., "Therapy of Tuberculosis in Mice by DNA Vaccination", Nature, vol. 400, No. 6741, pp. 269-271, Jul. 15, 1999.

H Hauser et al., Secretory heat-shock protein as a dendritic cell-targeting molecule: a new strategy to enhance the potency of genetic vaccines, Gene Therapy (2004) 11, 924-932.

* cited by examiner

SEQUENCE LISTING

```
<160> NUMBER OF SEQ ID NOS: 24

<210> SEQ ID NO 1
<211> LENGTH: 30
<212> TYPE: DNA
<213> ORGANISM: Artificial
<220> FEATURE:
<223> OTHER INFORMATION: Designed oligonucleotide primer for PCR

<400> SEQUENCE: 1
tggcgctagc atggaaaccc tttgcctcag                                          30

<210> SEQ ID NO 2
<211> LENGTH: 33
<212> TYPE: DNA
<213> ORGANISM: Artificial
<220> FEATURE:
<223> OTHER INFORMATION: Designed oligonucleotide primer for PCR

<400> SEQUENCE: 2
tggcgtcgac gttcatgctg tcgtccttat ggc                                      33

<210> SEQ ID NO 3
<211> LENGTH: 1281
<212> TYPE: DNA
<213> ORGANISM: Homo sapiens

<400> SEQUENCE: 3
atggaaaccc tttgcctcag ggcatccttt tggctggcac tggttggatg tgtaatcagt          60
gataatcctg agagatacag cacaaatcta agcaatcatg tggatgattt caccactttt         120
cgtggcacag agctcagctt cctggttacc actcatcaac ccactaattt ggtcctaccc         180
agcaatggct caatgcacaa ctattgccca cagcagacta aaattacttc agctttcaaa         240
tacattaaca ctgtgatatc ttgtactatt ttcatcgtgg aatggtggg  gaatgcaact         300 ctgctcagga tcatttacca gaacaaatgt atgaggaatg ccccaacgc  gctgatagcc         360 agtcttgccc ttggagacct tatctatgtg gtcattgatc tccctatcaa tgtatttaag         420
ctgctggctg ggcgctggcc ttttgatcac aatgactttg gcgtatttct ttgcaagctg         480
ttcccctttt tgcagaagtc ctcggtgggg atcaccgtcc tcaacctctg cgctcttagt         540
gttgacaggt acagagcagt tgcctcctgg agtcgtgttc agggaattgg gattcctttg         600
gtaactgcca ttgaaattgt ctccatctgg atcctgtcct ttatcctggc cattcctgaa         660
gcgattggct tcgtcatggt acccttgaa tataggggtg aacagcataa aacctgtatg         720
ctcaatgcca catcaaaatt catggagttc taccaagatg taaaggactg gtggctcttc         780
```

```
gggttctatt tctgtatgcc cttggtgtgc actgcgatct tctacaccct catgacttgt    840
gagatgttga acagaaggaa tggcagcttg agaattgccc tcagtgaaca tcttaagcag    900
cgtcgagaag tggcaaaaac agttttctgc ttggttgtaa ttttttgctct ttgctggttc   960 cctcttcatt taagccgtat attgaagaaa actgtgtata acgagatgga caagaaccga   1020
tgtgaattac ttagtttctt actgctcatg gattacatcg gtattaactt ggcaaccatg   1080
aattcatgta taaaccccat agctctgtat tttgtgagca agaaatttaa aaattgtttc   1140
cagtcatgcc tctgctgctg ctgttaccag tccaaaagtc tgatgacctc ggtccccatg   1200
aacggaacaa gcatccagtg gaagaaccac gatcaaaaca accacaacac agaccggagc   1260
agccataagg acagcatgaa c                                             1281
```

<210> SEQ ID NO 4
<211> LENGTH: 39
<212> TYPE: DNA
<213> ORGANISM: Artificial
<220> FEATURE:
<223> OTHER INFORMATION: Designed oligonucleotide primer for PCR

<400> SEQUENCE: 4

```
tggcgtcgac ctattagttc atgctgtcgt ccttatggc                            39
```

<210> SEQ ID NO 5
<211> LENGTH: 30
<212> TYPE: DNA
<213> ORGANISM: Artificial
<220> FEATURE:
<223> OTHER INFORMATION: Designed oligonucleotide primer for PCR

<400> SEQUENCE: 5

```
tggcgtcgac atggaaaccc tttgcctcag                                      30
```

<210> SEQ ID NO 6
<211> LENGTH: 60
<212> TYPE: DNA
<213> ORGANISM: Artificial
<220> FEATURE:
<223> OTHER INFORMATION: Designed oligonucleotide primer for PCR

<400> SEQUENCE: 6

```
tggcaagctt ctattacttg tcgtcgtcgt cgtagtcgtt catgctgtcg tccttatggc     60
```

<210> SEQ ID NO 7
<211> LENGTH: 7
<212> TYPE: PRT
<213> ORGANISM: Artificial
<220> FEATURE:
<223> OTHER INFORMATION: FLAG peptide

<400> SEQUENCE: 7

Asp Tyr Asp Asp Asp Asp Lys
1               5

<210> SEQ ID NO 8
<211> LENGTH: 33
<212> TYPE: DNA
<213> ORGANISM: Artificial
<220> FEATURE:
<223> OTHER INFORMATION: Designed oligonucleotide primer for PCR

<400> SEQUENCE: 8

```
tggcgtcgac atggcagcta aagacgtaaa att                                  33
```

```
<210> SEQ ID NO 9
<211> LENGTH: 37
<212> TYPE: DNA
<213> ORGANISM: Artificial
<220> FEATURE:
<223> OTHER INFORMATION: Designed oligonucleotide primer for PCR

<400> SEQUENCE: 9
tggcctatta gcggccgcca tcatgccgcc catgcca                        37

<210> SEQ ID NO 10
<211> LENGTH: 1647
<212> TYPE: DNA
<213> ORGANISM: Escherichia coli

<400> SEQUENCE: 10
atggcagcta aagacgtaaa attcggtaac gacgctcgtg tgaaaatgct gcgcggcgta    60
aacgtactgg cagatgcagt gaaagttacc ctcggtccaa aaggccgtaa cgtagttctg   120
gataaatctt tcggtgcacc gaccatcacc aaagatggtg tttccgttgc tcgtgaaatc   180
gaactggaag acaagttcga aaatatgggt gcgcagatgg tgaaagaagt gcctctaaa    240 gcaaacgacg ctgcaggcga cggtaccacc actgcaaccg tactggctca ggctatcatc   300
actgaaggtc tgaaagctgt tgctgcgggc atgaacccga tggacctgaa acgtggtatc   360
gacaaagcgg ttaccgctgc agttgaagaa ctgaaagcgc tgtccgtacc atgctctgac   420
tctaaagcga ttgctcaggt tggtaccatc tccgctaact ccgacgaaac cgtaggtaaa   480
ctgatcgctg aagcgattga caaagtcggt aagaaggcg ttatcaccgt tgaagacggt   540
accggtctgc aggacgaact ggacgtggtt gaaggtatgc agttcgaccg tggctacctg   600
tctccttact tcatcaacaa gccggaaact ggcgcagtag aactggaaag cccgttcatc   660
ctgctggctg acaagaaaat ctccaacatc cgcgaaatgc tgccggttct ggaagctgtt   720
gccaaagcag gcaaaccgct gctgatcatc gctgaagatg tagaaggcga agcgctggca   780
actctggttg ttaacaccat gcgtggcatc gtgaaagtcg ctgcggttaa agcaccgggc   840
ttcggcgatc gtcgtaaagc tatgctgcag gatatcgcaa ccctgactgg cggtaccgtg   900
atctctgaag agatcggtat ggagctggaa aaagcaaccc tggaagacct gggtcaggct   960
aaacgtgttg tgatcaacaa agacaccacc actatcatcg atggcgtggg tgaagaagct  1020
gcaatccagg gccgtgttgc tcagatccgt cagcagattg aagaagcaac ttctgactac  1080
gaccgtgaaa aactgcagga acgcgtagcg aaactggcag gcggcgttgc agttatcaaa  1140
gtgggtgctg ctaccgaagt tgaaatgaaa gagaaaaaag cacgcgttga agatgccctg  1200
cacgcgaccc gtgctgcggt agaagaaggc gtggttgctg gtggtggtgt tgcgctgatc  1260
cgcgtagcgt ctaaactggc tgacctgcgt ggtcagaacg aagaccagaa cgtgggtatc  1320
aaagttgcac tgcgtgcaat ggaagctccg ctgcgtcaga tcgtattgaa ctgcggcgaa  1380
gaaccgtctg ttgttgctaa caccgttaaa ggcggcgacg gcaactacgg ttacaacgca  1440
gcaaccgaag aatacggcaa catgatcgac atgggtatcc tggatccaac caaagtaact  1500
cgttctgctc tgcagtacgc agcttctgtg gctggcctga tgatcaccac cgaatgcatg  1560
gttaccgacc tgccgaaaaa cgatgcagct gacttaggcg ctgctggcgg tatgggcggc  1620
atgggtggca tgggcggcat gatgtaa                                     1647

<210> SEQ ID NO 11
<211> LENGTH: 102
<212> TYPE: DNA
<213> ORGANISM: Artificial
```

```
<220> FEATURE:
<223> OTHER INFORMATION: Designed oligonucleotide linker

<400> SEQUENCE: 11
catgggctct agaggtggtg gtagcggtgg tggtagcgct agccccgacc cgactcgagg      60
gtggtggtag cgattataaa gatgatgatg ataaataata ga                       102

<210> SEQ ID NO 12
<211> LENGTH: 102
<212> TYPE: DNA
<213> ORGANISM: Artificial
<220> FEATURE:
<223> OTHER INFORMATION: Designed oligonucleotide linker

<400> SEQUENCE: 12
agcttctatt atttatcatc atcatcttta atcgctac caccaccctc gagtcgggtc       60
ggggctagcg ctaccaccac cgctaccacc acctctagag cc                       102

<210> SEQ ID NO 13
<211> LENGTH: 42
<212> TYPE: DNA
<213> ORGANISM: Artificial
<220> FEATURE:
<223> OTHER INFORMATION: Designed oligonucleotide primer for PCR

<400> SEQUENCE: 13
agccactagt gcagctaaag acgtaaaatt cggtaacgac gc                        42

<210> SEQ ID NO 14
<211> LENGTH: 30
<212> TYPE: DNA
<213> ORGANISM: Artificial
<220> FEATURE:
<223> OTHER INFORMATION: Designed oligonucleotide primer for PCR

<400> SEQUENCE: 14
tgcctctaga caggtcggta accatgcatt                                      30

<210> SEQ ID NO 15
<211> LENGTH: 73
<212> TYPE: DNA
<213> ORGANISM: Artificial
<220> FEATURE:
<223> OTHER INFORMATION: Designed oligonucleotide linker

<400> SEQUENCE: 15
gtgcaatgga agctccgctg gagcagatcg tattgaactg cggcgaagcg ccggcagctg     60
ttgctaacac cgt                                                        73

<210> SEQ ID NO 16
<211> LENGTH: 78
<212> TYPE: DNA
<213> ORGANISM: Artificial
<220> FEATURE:
<223> OTHER INFORMATION: Designed oligonucleotide linker

<400> SEQUENCE: 16
taacggtgtt agcaacagct gccggcgctt cgccgcagtt caatacgatc tgctccagcg     60
gagcttcatg tgcacgca                                                   78

<210> SEQ ID NO 17
<211> LENGTH: 29
<212> TYPE: DNA
<213> ORGANISM: Artificial
```

```
<220> FEATURE:
<223> OTHER INFORMATION: Designed oligonucleotide primer for PCR

<400> SEQUENCE: 17
acggctagca tggaaccct ttgcctcag                                  29

<210> SEQ ID NO 18
<211> LENGTH: 29
<212> TYPE: DNA
<213> ORGANISM: Artificial
<220> FEATURE:
<223> OTHER INFORMATION: Designed oligonucleotide primer for PCR

<400> SEQUENCE: 18
acgctcgagg ttcatgctgt ccttatggc                                 29

<210> SEQ ID NO 19
<211> LENGTH: 29
<212> TYPE: DNA
<213> ORGANISM: Artificial
<220> FEATURE:
<223> OTHER INFORMATION: Designed oligonucleotide primer for PCR

<400> SEQUENCE: 19
agcgctagca tggaaccct ttgcctcag                                  29

<210> SEQ ID NO 20
<211> LENGTH: 30
<212> TYPE: DNA
<213> ORGANISM: Artificial
<220> FEATURE:
<223> OTHER INFORMATION: Designed oligonucleotide primer for PCR

<400> SEQUENCE: 20
tgcctcgagt cagttcatgc tgtccttatg                                30

<210> SEQ ID NO 21
<211> LENGTH: 28
<212> TYPE: DNA
<213> ORGANISM: Artificial
<220> FEATURE:
<223> OTHER INFORMATION: Designed oligonucleotide primer for PCR

<400> SEQUENCE: 21
agcgctagca tgcagccgcc tccaagtc                                  28

<210> SEQ ID NO 22
<211> LENGTH: 37
<212> TYPE: DNA
<213> ORGANISM: Artificial
<220> FEATURE:
<223> OTHER INFORMATION: Designed oligonucleotide primer for PCR

<400> SEQUENCE: 22
tgcctcgagc tattaagatg agctgtattt attactg                        37

<210> SEQ ID NO 23
<211> LENGTH: 1329
<212> TYPE: DNA
<213> ORGANISM: Homo sapiens

<400> SEQUENCE: 23
atgcagccgc ctccaagtct gtgcggacgc gccctggttg cgctggttct tgcctgcggc    60
ctgtcgcgga tctggggaga ggagagaggc ttccgcctg acagggccac tccgcttttg   120
caaaccgcag agataatgac gccacccact aagaccttat ggcccaaggg ttccaacgcc   180
```

```
agtctggcgc ggtcgttggc acctgcggag gtgcctaaag gagacaggac ggcaggatct      240
ccgccacgca ccatctcccc tcccccgtgc caaggaccca tcgagatcaa ggagactttc      300
aaatacatca acacggttgt gtcctgcctt gtgttcgtgc tggggatcat cgggaactcc      360
acacttctga gaattatcta caagaacaag tgcatgcgaa acggtcccaa tatcttgatc      420
gccagcttgg ctctgggaga cctgctgcac atcgtcattg acatccctat caatgtctac      480
aagctgctgg cagaggactg gccatttgga gctgagatgt gtaagctggt gcctttcata      540
cagaaagcct ccgtgggaat cactgtgctg agtctatgtg ctctgagtat tgacagatat      600
cgagctgttg cttcttggag tagaattaaa ggaattgggg ttccaaaatg gacagcagta      660
gaaattgttt tgatttgggt ggtctctgtg gttctggctg tccctgaagc cataggtttt      720
gatataatta cgatggacta caaaggaagt tatctgcgaa tctgcttgct tcatcccgtt      780
cagaagacag cttcatgca gttttacaag acagcaaaag attggtggct gttcagtttc       840
tatttctgct tgccattggc catcactgca ttttttttata cactaatgac ctgtgaaatg      900
ttgagaaaga aaagtggcat gcagattgct ttaaatgatc acctaaagca gagacgggaa      960
gtggccaaaa ccgtcttttg cctggtcctt gtctttgccc tctgctggct tccccttcac     1020
ctcagcagga ttctgaagct cactctttat aatcagaatg atcccaatag atgtgaactt     1080
ttgagctttc tgttggtatt ggactatatt ggtatcaaca tggcttcact gaattcctgc     1140
attaacccaa ttgctctgta tttggtgagc aaaagattca aaaactgctt taagtcatgc     1200
ttatgctgct ggtgccagtc atttgaagaa aaacagtcct tggaggaaaa gcagtcgtgc     1260
ttaaagttca aagctaatga tcacggatat gacaacttcc gttccagtaa taaatacagc     1320
tcatcttaa                                                             1329

<210> SEQ ID NO 24
<211> LENGTH: 1647
<212> TYPE: DNA
<213> ORGANISM: Escherichia coli

<400> SEQUENCE: 24
atggcagcta aagacgtaaa attcggtaac gacgctcgtg tgaaaatgct gcgcggcgta       60
aacgtactgg cagatgcagt gaaagttacc ctcggtccaa aaggccgtaa cgtagttctg      120
gataaatctt cggtgcacc gaccatcacc aaagatggtg tttccgttgc tcgtgaaatc       180
gaactggaag acaagttcga aaatatgggt gcgcagatgg tgaaagaagt tgcctctaaa      240
gcaaacgacg ctgcaggcga cggtaccacc actgcaaccg tactggctca ggctatcatc      300
actgaaggtc tgaaagctgt tgctgcgggc atgaacccga tggacctgaa acgtggtatc      360
gacaaagcgg ttaccgttgc agttgaagaa ctgaaagcgc tgtccgtacc atgctctgac      420
tctaaagcga ttgctcaggt tggtaccatc tccgctaact ccgacgaaac cgtaggtaaa      480
ctgatcgctg aagcgatgga caaagtcggt aaagaaggcg ttatcaccgt tgaagacggt      540
accggtctgc aggacgaact ggacgtggtt gaaggtatgc agttcgaccg tggctacctg      600
tctccttact tcatcaacaa gccggaaact ggcgcagtag aactggaaag cccgttcatc      660
ctgctggctg acaagaaaat ctccaacatc cgcgaaatgc tgccggttct ggaagctgtt      720
gccaaagcag gcaaaccgct gctgatcatc gctgaagatg tagaaggcga agcgctggca      780
actctggttg ttaacaccat gcgtggcatc gtgaaagtcg ctgcggttaa agcaccgggc      840
ttcggcgatc gtcgtaaagc tatgctgcag gatatcgcaa ccctgactgg cggtaccgtg      900
atctctgaag agatcggtat ggagctggaa aaagcaaccc tggaagacct gggtcaggct      960
```

```
aaacgtgttg tgatcaacaa agacaccacc actatcatcg atggcgtggg tgaagaagct    1020
gcaatccagg gccgtgttgc tcagatccgt cagcagattg aagaagcaac ttctgactac    1080
gaccgtgaaa aactgcagga acgcgtagcg aaactggcag gcggcgttgc agttatcaaa    1140
gtgggtgctg ctaccgaagt tgaaatgaaa gagaaaaaag cacgcgttga agatgccctg    1200
cacgcgaccc gtgctgcggt agaagaaggc gtggttgctg gtggtggtgt tgcgctgatc    1260
cgcgtagcgt ctaaactggc tgacctgcgt ggtcagaacg aagaccagaa cgtgggtatc    1320
aaagttgcac tgcgtgcaat ggaagctccg ctggagcaga tcgtattgaa ctgcggcgaa    1380
gcgccggcag ctgttgctaa caccgttaaa ggcggcgacg gcaactacgg ttacaacgca    1440
gcaaccgaag aatacggcaa catgatcgac atgggtatcc tggatccaac caaagtaact    1500
cgttctgctc tgcagtacgc agcttctgtg gctggcctga tgatcaccac cgaatgcatg    1560
gttaccgacc tgccgaaaaa cgatgcagct gacttaggcg ctgctggcgg tatgggcggc    1620
atgggtggca tgggcggcat gatgtaa                                        1647
```

METHOD OF IMMUNIZING ANIMAL, COMPOSITION FOR IMMUNIZATION, METHOD FOR PRODUCING ANTIBODY, METHOD FOR PRODUCING HYBRIDOMA AND METHOD FOR PRODUCING MONOCLONAL ANTIBODY

This application is a U.S. national stage of International Application No. PCT/JP2005/018953 filed Oct. 14, 2005.

TECHNICAL FIELD

The present invention relates to a method for immunizing an animal, a composition for immunization, a method for producing an antibody, a method for producing a hybridoma, and a method for producing a monoclonal antibody. More particularly, it relates to a method for immunizing an animal inducing a humoral immune response by administering a fusion gene composed of a gene encoding an antigen protein and a gene encoding a chaperonin, a composition for immunization for use in the method for immunization, a method for producing an antibody using the method for immunizing, a method for producing a hybridoma using an immune cell of an animal immunized by the method for immunizing, and a method for producing a monoclonal antibody using the hybridoma.

BACKGROUND ART

An antibody is a principal player in humoral immunity and takes an important role in biological defense a s well as a sensitized lymphocyte. Meanwhile, an antibody is frequently used for various kinds of techniques that take advantage of a specific affinity with its antigen, such as affinity chromatography or immunoassays, being indispensable tools in the biotechnology field. Consequently, an antibody is prepared by administering an antigen protein to an animal as an immunogen to induce a humoral immune response. At this time, the antigen protein isolated and purified from a sample such as a biological sample is used as an immunogen, for example. Recently, it is commonly practiced to introduce a gene encoding an antigen protein into a host cell by means of recombinant DNA techniques so as to isolate and purify a recombinant protein from a cultured broth of the host cell. When it is difficult to prepare an antigen protein by means of recombinant DNA techniques, it is also practiced to chemically synthesize a peptide corresponding to a part of the antigen protein and administer the synthesized peptide to the animal as an immunogen.

On the other hand, there is a technique called gene immunization, in which a gene encoding an antigen protein is expressed in the animal to induce an immune response in stead of inoculating the antigen protein. In carrying out gene immunization, a gene encoding an antigen protein is integrated in an appropriate expression vector, for example, so as to inoculate the expression vector to the animal, whereupon the gene integrated in the expression vector is expressed in the animal to synthesize an antigen protein. As a consequence, the antigen protein synthesized in the animal induces an immune response. According to gene immunization, as long as a gene encoding an antigen protein is isolated, immunization is carried out, dispensing with isolation and purification of the antigen protein. Consequently, it is possible to induce an immune response to the antigen protein even if its purification method is unestablished, its purification is difficult, or it is an unknown antigen protein with only its gene being known. That makes it possible to obtain an antibody against such an antigen protein. Further, gene immunization has the additional advantage of being able to induce an immune response even if the amount of an antigen protein synthesized by expression of a gene in the animal is far small than that required for direct administration of the antigen protein. It has further the additional advantage that there is no need to chemically synthesize a peptide antigen separately as in the conventional ways even if an antigen protein is difficult to be prepared by recombinant DNA techniques and that it is only necessary to introduce the full length of a gene into the animal.

As described above, although gene immunization has advantages not shared by the conventional ways, a humoral immune response may not be induced depending on the kind of the antigen protein, resulting in possibly failing to produce an antibody. In the following examples, a humoral immune response may not be induced as well as in the conventional method for immunizing. Specifically, in the case that an antigen protein has extremely high homology to a protein contained endogenously in an immunized animal, the antigen protein is not recognized as a foreign body even though being synthesized in the animal, resulting in possibly failing to induce a humoral immune response. Further, in the case that an antigen protein is labile in the animal, the antigen protein in the animal becomes less in amount, resulting in possibly failing to induce a humoral immune response. Still further, in the case that an antigen protein mainly induces cellular immunity, humoral immunity is difficult to be induced. Yet further, gene immunization has a specific disadvantage of possibly failing to induce humoral immune response due to less amount of an antigen protein resulting from the case that a transduction efficiency of a gene encoding the antigen protein into the animal is low or that expression level of a gene encoding the antigen protein in the animal is low.

In order to solve the problems and drawbacks described above of gene immunization, various ingenuities have been proposed. There is an example (patent document 1) that, in induction of an immune response to urokinase, administration of a urokinase gene in the form of a fusion gene combined with a transmembrane domain gene, instead of administration of the urokinase gene alone, induces a high immune response to urokinase, so as to obtain an antibody against urokinase. It is thought that the high immune response obtained herein is induced because the urokinase region in a fusion protein that is an expression product of the fusion gene is compulsorily arranged on the cell surface.

In the field of vaccines, there is an example (patent document 2) that a fusion gene (chimeric nucleic acid) composed of a gene encoding a heat-shock protein HSP70 and a gene encoding an antigen protein is used as a DNA vaccine. In this example, a gene encoding HSP70 derived from Mycobacterium tuberculosis is used. However, this technique induces antigen-specific cellular immunity (killer T-cell), but does not induce humoral immunity, or antibody production. Meanwhile, there is a report (patent document 3) that the use of a fusion protein composed of HSP70 derived from Mycobacterium tuberculosis and an antigen protein as an immunogen makes the HSP70 to function as a suitable adjuvant and induces antibody production against the antigen protein. These mean that an immune response by a fusion protein composed of HSP70 and an antigen protein has a different mechanism in antigen-presenting cells from an immune response by a fusion gene composed of HSP70 gene and an antigen protein gene. In this way, in the case of induction of a humoral immune response to an antigen protein, immunization using a gene of the antigen protein may not always induce a desired immune response. It is considered to be even higher possible that a desired immune response to the antigen protein is not induced.

Patent document 1: WO 02/08416
Patent document 2: WO 01/29233
Patent document 3: WO 94/29459

SUMMARY OF THE INVENTION

Problems to be Solved by the Invention

As described above, gene immunization still has the large state of the unknown and is still in the process of trial and error. Preparation of an antibody by gene immunization requires such a technique as being capable of induce a humoral immune response reproducibly and certainly regardless of the kinds of antigen proteins. It is therefore an object of the present invention to provide various techniques capable of inducing a humoral immune response with higher efficiency in preparation of an antibody against an antigen protein by means of gene immunization.

Means to Solve the Problems

The inventors have found that even an antigen protein that is not able to induce a humoral immune response by inoculation of its gene to an animal induces a humoral immune response to the antigen protein by inoculation of a fusion gene composed of a gene encoding the antigen protein and a gene encoding a chaperonin to the animal, and have achieved the present invention. The following description is a summary of the present invention.

The first aspect of the present invention is a method for immunizing an animal, including the step of administering a fusion gene to an animal, the fusion gene being composed of a gene encoding the full-length or a part of an antigen protein and a gene encoding one selected from a chaperonin subunit and a chaperonin subunit linkage linked thereto, so as to express the fusion gene in the animal to induce a humoral immune response to the antigen protein.

The method for immunizing an animal of this aspect belongs to gene immunization and is performed by administering a fusion gene to an animal, the fusion gene being composed of a gene encoding the full-length or a part of an antigen protein and a gene encoding a chaperonin subunit or a chaperonin subunit linkage linked thereto. Thus, the fusion gene is expressed in the animal, so that a fusion protein composed of the full-length or a part of the antigen protein and the gene encoding the chaperonin subunit or the chaperonin subunit linkage is synthesized. As a result, a humoral immune response to the antigen protein is induced. According to the method of this aspect, a humoral immune response is induced by a chaperonin even if the antigen protein is not able to induce a humoral immune response by administering a gene encoding the antigen protein alone. Consequently, an antibody against such an antigen protein is produced in an animal.

Chaperonins are a kind of molecular chaperones and are complex proteins composed of subunits (chaperonin subunits) each with a molecular weight of about 60,000. Chaperonins accommodate and fold correctly other proteins therewithin. A "chaperonin subunit linkage" is defined as an artificial protein composed of more than one chaperonin subunit serially linked via a peptide bond. In other words, a chaperonin subunit linkage is an artificial protein composed of more than one tandemly-linked chaperonin subunit. Herein, in the present specification, a gene encoding a chaperonin subunit and a gene encoding a chaperonin subunit linkage are sometimes collectively referred to as a "gene encoding a chaperoning".

Preferably, one selected from the chaperonin subunit and the chaperonin subunit linkage is derived from *Escherichia coli*.

A chaperonin derived from *E. coli* is referred to as GroEL, whose biochemical and physiochemical attribute is well studied, and thus its gene is easily available. In the method in this preferred aspect, the chaperonin subunit or the chaperonin subunit linkage is derived from *E. coli*. This constitution readily produces a fusion gene to be administered to an animal.

Preferably, the fusion gene is integrated into an expression vector and expressed under control of a promoter on the expression vector.

In the method in this preferred aspect, the fusion gene is integrated into an expression vector and expressed under control of a promoter on the expression vector. According to this constitution, a fusion gene is expressed in the animal more certainly. Consequently, a humoral immune response is induced more certainly.

Preferably, the promoter is one selected from the group consisting of a CMV promoter, an AML promoter, an SV40 promoter, an SRα promoter, and an EF-1α promoter.

In the method in this preferred aspect, the promoter on the expression vector is a promoter such as a CMV promoter which has high inductivity and whose attribute is well known. According to this constitution, a fusion gene is highly efficiently expressed. Consequently, a humoral immune response is induced more certainly.

Preferably, the expression vector contains a CpG motif.

A CpG motif is a sequence contained in DNA of microorganism and known to enhance an immunostimulating system of mammals. In the method in this preferred aspect, the expression vector contains a CpG motif. This constitution induces a higher humoral immune response to an animal. Consequently, an antibody against an antigen protein is highly efficiently produced.

Preferably, the animal is one selected from a mammal and a bird.

In the method in this preferred aspect, an animal to be immunized is a mammal or a bird, which is easy to use. According to this constitution, immunization is carried out more readily.

Preferably, the mammal is one selected from the group consisting of a mouse, a rat, a rabbit, a bovine, a horse, a dog, a cat, a goat, a sheep, and a pig. Preferably, the bird is one selected from the group consisting of a chicken, a duck, and a turkey.

The antigen protein is preferably one selected from the group consisting of a G protein-coupled receptor, an ion channel-linked receptor, a tyrosine kinase-type receptor, a CD antigen, a cell adhesion molecule, a cancer antigen, a cytokine, a growth factor, a trophic factor, a viral antigen, a bacterial antigen, and a toxic antigen.

In the method in this preferred aspect, the antigen protein is a protein useful for drug development such as a G protein-coupled receptor. According to this constitution, an antibody against the useful protein is obtained and applied for construction of an assay system or the like.

The second aspect of the present invention is a composition for immunization for use in the method for immunizing an animal of the present invention, including a fusion gene composed of a gene encoding the full-length or a part of an antigen protein and a gene encoding one selected from a chaperonin subunit and a chaperonin subunit linkage linked thereto as a main ingredient.

When the method for immunizing an animal of the present invention is embodied, a composition is prepared by dissolving a fusion gene in an appropriate solvent, for example, so as to be administered to an animal. The composition for immunization of this aspect is used for the method for immunizing an animal of the present invention and includes a fusion gene composed of a gene encoding the full-length or a part of an antigen protein and a gene encoding a chaperonin subunit or a chaperonin subunit linkage linked thereto as a main ingredient. According to the composition of this aspect, a fusion gene is administered to an animal by means such as injection. Further, applied dose of the fusion gene is precisely adjusted by control of concentration of the fusion gene in the composition.

The third aspect of the present invention is a method for producing an antibody, including the steps of immunizing an animal by means of the method for immunizing an animal of the present invention to induce a humoral immune response to an antigen protein, so that an antibody against the antigen protein is produced in the animal, and obtaining the antibody from the animal.

The above-mentioned method for immunizing an animal of the present invention induces a humoral immune response, with the consequence that an antibody is produced in the animal. The method for producing an antibody of this aspect is carried out in such a manner that a humoral immune response is induced by the method for immunizing an animal of the present invention to produce an antibody against an antigen protein in the animal, from which the antibody is obtained. According to the method of this aspect, an antibody is produced in an animal even if an antigen protein, whose purification method is unestablished, whose purification is difficult, or that is unknown with only its gene being known, does not produce an antibody by administration of its gene alone. The antibody is obtained as a polyclonal antibody from a serum of the animal.

The fourth aspect of the present invention is a method for producing a hybridoma, including the steps of immunizing an animal by the method for immunizing an animal of the present invention to induce a humoral immune response to an antigen protein, obtaining an immunocyte from the animal, and fusing the immunocyte and a myeloma, so as to prepare a hybridoma producing an antibody against the antigen protein.

In the method for producing a hybridoma of this aspect, a hybridoma producing a monoclonal antibody against an antigen protein is prepared by cell fusion of an immunocyte of an animal, in which a humoral immune response is induced by the method for immunizing an animal of the present invention, and a myeloma. According to this constitution, even if an antigen protein does not produce an antibody by administration of the antigen protein itself or its gene alone, a hybridoma producing a monoclonal antibody against the antigen protein is obtained.

The fifth aspect of the present invention is a method for producing a monoclonal antibody, including the steps of culturing the hybridoma produced by the method of the present invention and obtaining a monoclonal antibody against the antigen protein from the culture of the hybridoma.

In the method for producing a monoclonal antibody of this aspect, a hybridoma produced by the method for producing a hybridoma of the present invention is cultured, whereupon a monoclonal antibody is obtained from the culture. According to this constitution, even if an antigen protein does not produce an antibody by administration of the antigen protein itself or its gene alone, a hybridoma producing a monoclonal antibody against the antigen protein is obtained.

The sixth aspect of the present invention is a method for producing a monoclonal antibody, including the steps of immunizing an animal by the method for immunizing an animal of the present invention to induce a humoral immune response to an antigen protein, preparing mRNA against an antibody from the animal, and preparing cDNA from the mRNA used as a template, so that a monoclonal antibody against the antigen protein is prepared by a phage display method using the cDNA.

The method for producing a monoclonal antibody of this aspect uses a phage display method. MRNA is prepared from an animal, in which a humoral immune response is induced by the method for immunizing an animal of the present invention, whereupon cDNA is prepared from the MRNA used as a template, so that a monoclonal antibody against the antigen protein is prepared by a phage display method using the cDNA. According to this constitution, even if an antigen protein does not produce an antibody by administration of the antigen protein or its gene alone, a monoclonal antibody against the antigen protein is obtained.

ADVANTAGEOUS EFFECT OF THE INVENTION

According to the method for immunizing an animal and the composition for immunization of the present invention, a humoral immune response is induced in gene immunization even if an antigen protein does not induce a humoral immune response by injection of its gene alone to an animal.

According to the method for producing an antibody of the present invention, an antibody against an antigen protein is produced in gene immunization even if the antigen protein does not induce a humoral immune response by injection of its gene alone to an animal.

According to the method for producing a hybridoma of the present invention, a hybridoma producing a monoclonal antibody against an antigen protein is produced in gene immunization even if the antigen protein does not induce a humoral immune response by injection of its gene alone to an animal.

According to the method for producing a monoclonal antibody of the present invention, a monoclonal antibody against an antigen protein is produced in gene immunization even if the antigen protein does not induce a humoral immune response by injection of its gene alone to an animal.

DESCRIPTION OF THE PREFERRED EMBODIMENTS

Figure 1A:
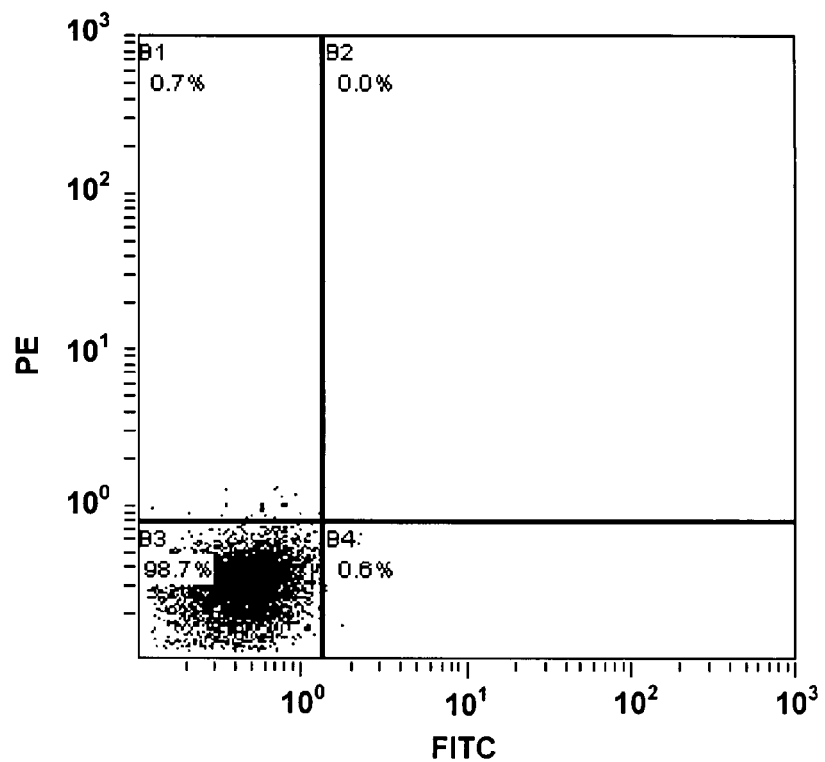
FIGS. 1A and 1B show analysis results of the interaction between HETAR gene-introduced cells and an anti-hETAR antibody in a serum in Example 3, FIG. 1A being a two-dimensional dot plot in the case of use of the serum before gene immunization (day 0), FIG. 1B being a two-dimensional dot plot in the case of use of the serum on the $35^{th}$ day after gene immunization.

Now, a preferred embodiment of the present invention will be described in detail below.

The method for immunizing an animal of the present invention belongs to gene immunization and is carried out by administering to an animal a fusion gene composed of a gene encoding the full-length or a part of an antigen protein and a gene encoding a chaperonin subunit or a chaperonin subunit linkage linked thereto. According to the method of the present invention, it is possible to use either a gene encoding the full-length of an antigen protein or a gene encoding a part of the antigen protein, whichever can be used in accordance with the intended use. A gene encoding the full-length of an antigen protein is suitable for producing, for example, an antibody against each of a plurality of epitopes contained in the antigen protein or an antibody recognizing a stereostructure of the antigen protein. A gene encoding a part of an antigen protein is suitable for producing, for example, an antibody against a specific epitope.

Chaperonins are a kind of molecular chaperones and are found in every living thing such as bacteria, archaea, and eukaryotes. Especially, they are found in large quantity in bacterial cytoplasm, eukaryotic cellular mitochondria, and chloroplasts. Chaperonins have an activity assisting protein folding or an activity preventing protein denaturation. Chaperonins are huge cylindrical complex proteins formed by two rings stacked on top of one another, each ring consisting of seven to nine chaperonin subunits (also referred to as Hsp60) each with a molecular weight of about 60,000, having a total molecular weight of about 800,000 to 1,000,000. Chaperonins each have a cavity within the rings, in which cavity folded intermediates of proteins or denatured proteins are transiently accommodated, so as to form a complex (hereinafter referred to as a "chaperonin-protein complex"). Then, it is known that the accommodated proteins are correctly folded in the cavity, whereupon the correctly folded proteins are released from the cavity.

Chaperonins are roughly divided into two types, group 1-type and group 2-type. Chaperonins found in bacteria and organelles in eukaryotic cells are classified in the group 1-type, requiring a circular complex of proteins with a molecular weight of about 10 kDa referred to as a co-chaperone as a cofactor. On the other hand, chaperonins found in eukaryotic cytoplasm and archaea are classified in the group 2-type, whose structure or function has a lot of unclear points, and which have not found a protein corresponding to a co-chaperone in the group 1-type (Gupta, Mol. Microbiol., 15, 1-, 1995). In the method for immunizing an animal of the present invention, a gene of any type of chaperonin can be used. For example, a chaperonin in the group 1-type includes *Escherichia coli* GroEL, whereas a chaperonin in the group 2-type includes TCP derived from archaea. More specifically, a gene encoding GroEL subunit or GroEL subunit linkage and a gene encoding TCP subunit or TCP subunit linkage can be used.

In an aspect of the method for immunizing an animal of the present invention, a fusion gene composed of a gene encoding the full-length or a part of an antigen protein and a chaperonin subunit is administered to an animal. That sufficiently induces a humoral immune response to the antigen protein even when a humoral immune response is not induced by a gene encoding the antigen protein alone. It is not well known about a form of an expression product of the fusion gene in the animal, but likely explanation is that chaperonins stabilize the antigen protein in cells of the immunized animal. Further, there is a report recently that chaperonins are bound to Toll-like receptor 2 and Toll-like receptor 4, which are antigen receptors in antigen-presenting cells (Gobert, A. P, et al., 2004, J. Biol. Chem. 279, 245). This shows that a chaperonin may function as a suitable adjuvant in fusion gene products composed of the chaperonin and a target antigen.

In another aspect of the method for immunizing an animal of the present invention, a fusion gene composed of a gene encoding the full-length or a part of an antigen protein and a gene encoding a chaperonin subunit linkage is administered to an animal. Herein, a "chaperonin subunit linkage" is defined as an artificial protein composed of more than one chaperonin subunit serially linked via a peptide bond. In other words, a chaperonin subunit linkage is an artificial protein composed of more than one tandemly-linked chaperonin subunit. Meanwhile, a gene encoding a chaperonin subunit linkage is an artificial gene composed of more than one chaperonin subunit gene serially linked. In other words, it is an artificial gene composed of more than one tandemly-linked chaperonin subunit gene. Of this aspect, a fusion gene composed of this artificial gene and a gene encoding an antigen protein is administered. Chaperonin subunit linkages are associated with one another to have the same complex structure as native chaperoning. Consequently, of this aspect, likely explanation is that an expression product of a fusion gene forms a complex as well as a native chaperonin-protein complex and that chaperonins stabilize the antigen protein in cells of the immunized animal. As described above, in the method for immunizing an animal of the present invention, it is considered that an antigen protein is accommodated in a chaperonin and occurs as a normal protein correctly folded.

A chaperonin derived from *E. coli* is referred to as GroEL. Structurally, GroEL is formed by two rings stacked on top of one another, each ring consisting of seven subunits (GroEL subunits), having a total of 14 subunits. A gene encoding a GroEL subunit is known and available, being suitable for carrying out the method of the present invention more simply. The known GroEL subunit gene has a nucleotide sequence shown in SEQ ID No. 10. A primer is designed based on the nucleotide sequence to carry out PCR using the genomic DNA of *E. coli* as a template, thereby obtaining a GroEL subunit gene.

Single-ring chaperonins formed by only one ring are also known. In the method for immunizing an animal of the present invention, a gene encoding a single-ring chaperonin is also available. Examples of a single-ring chaperonin include a modified GroEL subunit, which is given by substitution of a part of amino acid residues of a GroEL subunit. An example of a modified GroEL subunit gene is shown in SEQ ID No. 24. This modified GroEL subunit gene encodes a modified GroEL subunit (SR1), which is given by substitution of the amino acid residue 452 of the GroEL to a glutamic acid and of the amino acid residues 461, 463, and 464 to alanines.

Herein, a "gene encoding a chaperonin subunit" in the method of the present invention includes not only a gene encoding the full-length of a native chaperonin subunit but also a gene encoding a protein having the same activity derived from a native chaperonin subunit. Examples of such a gene include a gene encoding a mutant chaperonin subunit, which is given by modification of a native chaperonin subunit by means such as amino acid substitution. The examples further include a gene encoding a protein composed of a part of a domain of a native or the above-mentioned mutant chaperonin subunit. The examples still further include a gene encoding a protein, which is given by deletion of a part of a domain of a native or the above-mentioned mutant chaperonin subunit. For example, the use of a gene, which is given by deletion of a domain having high immunogeneity and being capable of becoming an antigenic determinant in a chaperonin subunit, performs operations such as prioritized induction of an immune response to an antigen protein.

The method of the present invention has such a preferred embodiment that a fusion gene is integrated into an expression vector and expressed under control of a promoter on the expression vector. An expression vector would be any expression vector replicable in animal cells and includes pCI, pSI, pAdVantage, pTriEX, pKA1, pCDM8, pSVK3, pMSG, pSVL, pBK-CMV, pBK-RSV, and EBV. A promoter on the expression vector would be any promoter functioning in animal cells and includes a CMV promoter in Cytomegarovirus (CMV), an AML promoter in Adenovirus Major Late (AML), an SV40 promoter in Simian Virus 40 (SV40), an SRα promoter (a fusion promoter composed of SV40 and HTLV-1 LTR), and an EF-1α promoter in Elongation Factor (EF). Further, the expression vector may contain an enhancer adapted to enhance a promoter activity.

Still further, the expression vector may contain a CpG motif. A CpG motif is a sequence rich in unmethylated cytosines (C) and guanines (G). A CpG motif is recognized by Toll like receptor 9 (TLR 9) occurring on the cell surface of an immunized animal, and activates an immune response by gene expression of cytokine via an intercellular signal transduction system and promotes expression of antigen information to enhance a specific immune response by antigen presentation and activation of helper T-cells. An expression vector containing a CpG motif gives a higher immune response by an effect enhancing an immunostimulatory system of the CpG motif. Herein, the CpG motif may be contained in any position in an expression vector and may be contained in one place or a plurality of places.

A method of administering a fusion gene in the method of the present invention is not particularly limited and includes a subcutaneous injection, an intramuscular injection, and an intravenous injection. Administration by a particle gun may be applicable. Fusion gene dosage in the method of the present invention may be appropriately determined depending on a condition such as the kind of a used expression vector or a used promoter, but approximately 1 to 3 mg/kg WT per dose. In the case of a mouse, it is 25 to 100 µg/dose. The number of doses may be one time, but multiple doses at predetermined intervals induce a higher humoral immune response.

An antigen protein suitable for the method of the present invention includes a G protein-coupled receptor, an ion channel-linked receptor, a tyrosine kinase-type receptor, a CD antigen, a cell adhesion molecule, a cancer antigen, a cytokine, a growth factor, a trophic factor, a viral antigen, a bacterial antigen, and a toxic antigen. Herein, the method of the present invention is carried out as long as any gene of these proteins is obtained, and it is not necessary to purify these proteins themselves.

An animal for use in the method of the present invention is preferably a mammal or a bird, which is easy to deal with. The mammal includes a mouse, a rat, a rabbit, a bovine, a horse, a dog, a cat, a goat, a sheep, and a pig. The bird includes a chicken, a duck, and a turkey. Especially, in order to finally obtain a monoclonal antibody, a mouse, a rat, a rabbit, or a chicken would be preferable due to its easiness of cell fusion. A monoclonal antibody is obtained as long as tumor cells of B-cells are obtained regardless of animal species.

A composition for immunization of the present invention has a fusion gene composed of a gene encoding the full-length or a part of an antigen protein and a gene encoding a chaperonin subunit or a chaperonin subunit linkage linked thereto as a main ingredient. A typical example of the composition of the present invention is given by dissolution of the fusion gene in an isotonic solution. The isotonic solution includes a physiological saline and a phosphate buffered saline (PBS). In addition, various kinds of buffer may be also used as a solvent. Addition of a metal ion such as $Mg^{2+}$ to an isotonic solution is effective in enhancing an ability to produce an antibody. Further, addition of an immunosuppressant specifically suppressing cellular immunity induces higher humoral immunity, thereby enhancing an ability to produce an antibody. Still further, addition of a cytokine such as GM-CSF, TNFα, or IL-4, which induces differentiation of $T_H2$ helper T-cells capable of inducing humoral immunity to an isotonic solution, or addition of a gene encoding any of these cytokines is also effective in enhancing an ability to produce an antibody. Similarly, addition of IL-10, one of cytokines, or a gene encoding IL-10 to an isotonic solution so as to suppress cellular immunity also induces humoral immunity, thereby enhancing an ability to produce an antibody. Further, addition of a cytokine such as IL-1, IL-2, IL-4, IL-5, IL-6, or IL-10, which induces activation of B-cells (a principal player in producing an antibody), division thereof, or differentiation thereof to antibody-producing cells, or addition of a gene encoding any of these cytokines to an isotonic solution enhances an ability to produce an antibody. A fusion gene in the composition of the present invention may be at a concentration of about 10 to 500 µg/mL.

Further, the composition for immunization of the present invention may contain an oligonucleotide composed of a CpG motif. In this case, the oligonucleotide functions as an adjuvant, so as to induce a higher immune response. The composition of the present invention can also used as a vaccine for inducing humoral immunity. When being used as a vaccine, the composition can be administered to humans.

According to a method for producing an antibody of the present invention, an antibody is obtained from an animal immunized by the method for immunizing an animal in the above-mentioned invention. Specifically, partial blood sampling from an immunized animal is carried out periodically to evaluate its antibody titer, whereby the status of antibody production is monitored. At the point when the antibody titer reaches the maximum level, whole blood sampling is carried out to prepare serum. Then, an antibody is obtained from the obtained serum. The antibody obtained in this time is a polyclonal antibody. Isolation and purification of an antibody from serum may be performed by a method generally used for purification of an antibody, and for example, by affinity chromatography using protein A.

According to a method for producing a hybridoma of the present invention, an immunocyte is obtained from an animal immunized by the method for immunizing an animal in the above-mentioned invention, whereupon the immunocyte and a myeloma are fused, so as to prepare a hybridoma. Cell fusion and selection and cloning of a hybridoma can be performed by the known method. Cell fusion can be performed by the method of Köhler-Milstein, for example. Selection of a hybridoma can be performed by culturing using a HAT selection medium. Cloning of a hybridoma can be performed by a limiting dilution method. Culturing of a hybridoma cloned in this way produces a monoclonal antibody against an antigen protein. Culturing of a hybridoma can be performed within an abdominal cavity of an animal such as a mouse or using a dish or the like in vitro. In the case of culturing a hybridoma within an abdominal cavity of an animal such as a mouse, ascites is obtained, and a monoclonal antibody is isolated and purified from the ascites. In the case of culturing in vitro, a monoclonal antibody is isolated and purified from the culture. A monoclonal antibody is purified by the above-mentioned affinity chromatography using protein A, for example, in the case of a monoclonal antibody with IgG subclass.

A method for producing a monoclonal antibody of the present invention includes a method using a phage display method. Specifically, mRNA is prepared from an animal immunized by the method for immunizing an animal in the above-mentioned invention, whereupon cDNA is prepared using the mRNA as a template, so that a single-chain antibody (scFv) gene encoding only an antibody variable region is prepared. The gene is cloned to a phagemid vector. E. coli, into which the phagemid vector is transduced, is infected with phage, so as to express the scFV antibody on the phage capsid. Screening of the scFv expressed in this way against an antigen protein prepares a monoclonal scFV antibody specific to the antigen protein. Herein, preparation of mRNA, preparation of cDNA, subcloning to phagemid or transduction to E. coli, phage infection, and screening of a monoclonal scFV antibody specific to an antigen protein each are performed by the known method. For example, subcloning of a scFV gene to a phagemid vector containing two elements consisting of a gene fragment encoding a leader sequence (signal sequence) and a phage capsid protein III and a replication origin of M13 and using of M13 phage as a phage are able to express a scFV antibody on the M13 phage. Further, a phage obtained by screening is infected to a specific bacterium and cultured, so that a monoclonal antibody specific to an antigen protein is also collected in large quantities from the culture. According to the method for producing a monoclonal antibody of the present invention, not only an scFV antibody but also an antibody fragment having no constant region such as an Fab antibody fragment are also prepared.

Hereafter, this invention will be described in more detail by reference to examples, but this invention is not limited to the examples.

EXAMPLE 1

(1) Isolation of a Human Endothelin A Receptor Gene

Gene immunization was carried out in the following procedures using human endothelin A receptor (HETAR) as a model antigen protein. First, PCR using a human lung cDNA library (Takara Bio) as a template and oligonucleotides as shown in SEQ ID No. 1 and No. 2 as a primer set was carried out, whereby a DNA fragment containing human endothelin A receptor (hETAR) gene as shown in SEQ ID No. 3 was amplified. Herein, an NheI site and an SalI site both derived from the primers were introduced into the amplified DNA fragment respectively at its 5'-terminus and its 3'-terminus. Similarly, PCR using oligonucleotides as shown in SEQ ID No. 1 and No. 4 as a primer set was carried out, whereby a DNA fragment containing an hETAR gene as shown in SEQ ID No. 3 was amplified. Herein, an NheI site, and an SalI site and a sequence encoding two termination codons (TAATAG) derived from the primers were introduced into the amplified DNA fragment respectively at its 5'-terminus and its 3'-terminus. Similarly, PCR using oligonucleotides as shown in SEQ ID No. 5 and No. 6 as a primer set was carried out, whereby a DNA fragment containing an HETAR gene as shown in SEQ ID No. 3 was amplified. Herein, an SalI site, and a sequence encoding a FLAG-tag (SEQ ID No. 7), a sequence encoding two termination codons (TAATAG), and an HindIII site derived from the primers were introduced into the amplified DNA fragment respectively at its 5'-terminus and its 3'-terminus.

(2) Isolation of a GroEL Subunit Gene

Genomic DNA was extracted and purified from Escherichia coli strain HMS174 (DE3) (Novagen). Then, PCR using the purified genomic DNA as a template and oligonucleotides as shown in SEQ ID No. 8 and No. 9 as a primer set was carried out, whereby a DNA fragment containing a GroEL subunit gene as shown in SEQ ID No. 10 was amplified. Herein, an SalI site, and an NotI site and a sequence encoding two termination codons (TAATAG) derived from the primers were introduced into the amplified DNA fragment respectively at its 5'-terminus and its 3'-terminus.

(3) Construction of a Vector for Gene Immunization Expressing a Fusion protein composed of human endothelin A receptor and a GroEL subunit An expression vector pCI Mammalian Expression Vector (Promega) was digested with restriction enzymes NheI and SalI and its termini were dephosphorylated by bacterial alkaline phosphatase (BAP), whereupon the amplified DNA fragment containing an hETAR gene in the above-mentioned step (1), into which an NheI site and an SalI site were introduced respectively at its 5'-terminus and its 3'-terminus, was introduced into the vector. Further, this expression vector was digested with SalI and NotI and its termini were dephosphorylated by BAP, whereupon the amplified DNA fragment containing the GroEL subunit gene in the above-mentioned step (2) was introduced, thereby constructing a vector pCI-hETAR-GroEL.

Specifically, the vector pCI-hETAR-GroEL had a fusion gene composed of a gene encoding HETAR and a gene encoding a GroEL subunit. Meanwhile, similarly, an expression vector pCI Mammalian Expression Vector was digested with restriction enzymes NheI and SalI and its termini were dephosphorylated by BAP, whereupon the amplified DNA fragment containing an HETAR gene in the above-mentioned step (1), into which an NheI site, and termination codons and an SalI site were introduced respectively at its 5'-terminus and its 3'-terminus, was introduced into the vector, thereby constructing a vector pCI-hETAR. Specifically, the vector pCI-hETAR had only an HETAR gene.

(4) Construction of a Vector Expressing Human Endothelin A Receptor

An expression vector pMAL (New England Biolabs) for E. coli was digested with restriction enzymes SalI and HindIII and its termini were dephosphorylated by BAP, whereupon the amplified DNA fragment containing an HETAR gene in the above-mentioned step (1), into which an SalI site, and a sequence encoding FLAG-tag, termination codons, and an HindIII site were introduced respectively at its 5'-terminus and its 3'-terminus, was introduced into the vector, thereby constructing an expression vector pMAL-hETAR. The expression vector pMAL-hETAR was capable of expressing a fusion protein composed of a maltose binding protein (MBP) and HETAR (hereinafter referred to as a "MBP-HETAR fusion protein) in E. coli.

(5) Preparation of Human Endothelin A Receptor

Human endothelin A receptor (antigen protein) for antibody detection was prepared in the following procedures. The expression vector pMAL-hETAR constructed in the above-mentioned step (4) was introduced into E. coli strain BL21 (Novagen) to give a transformant. The transformant was cultured at 25° C. and 110 rpm in 2×Y.T. medium (16 g/L Bacto-trypton, 10 g/L Yeast extract, and 5 g/L NaCl) for 18 hours. After having cultured, cells were recovered by centrifugation (30,000 g, for 30 minutes, 4° C.). The recovered cells were rinsed with PBS, suspended in PBS, and then disrupted by sonication. Insoluble precipitate was recovered by centrifugation (100,000 g, for an hour, 4° C.) from the disrupted cell suspension. The insoluble precipitate was dissolved in 4% Triton X-100, and then, subjected to SDS-PAGE analysis. Further, Western blot analysis using an anti-FLAG antibody (ANTI-FLAG M2 Monoclonal Antibody, Sigma) as a primary antibody was carried out. PVDF membrane (Immobilon-P Millipore) was used for blotting and a biotin-labeled universal secondary antibody kit (Universal Quick Kit, Vector Laboratories) was used as a secondary antibody. Konica Immunostain HRP-100 (Seikagaku) was used for detection. As a control, similar operations were carried out on a plasmid pMAL into which a gene encoding hETAR was not introduced. As a result, a band was detected at a position corresponding to a molecular weight of MBP-HETAR fusion protein (84 kDa), which was not detected in the control. That revealed that the full-length of HETAR was obtained.

(6) Gene Immunization

A vector pCI-hETAR-GroEL was dissolved in saline so as to be at a concentration of 250 μg/mL, and whereby a composition for immunization was prepared. The composition for immunization was injected to femoral muscles of both legs of a BALB/c mouse aged 8 weeks (female), 0.12 mL to each, so as to immunize the mouse (day 0). Thereby, 30 μg of pCI-hETAR-GroEL was administered to each of the both legs, that is, 60 μg for one mouse per dose. Thereafter, immunization was repeatedly performed in a similar fashion on the $7^{th}$ day, the $21^{st}$ day, and the $28^{th}$ day. Blood sampling was carried out on 0, the $7^{th}$, the $14^{th}$, the $21^{st}$, the $28^{th}$, the $35^{th}$, and the $42^{nd}$ days, so as to give sera. As a contrast, a mouse was immunized using a vector pCI-hETAR capable of expressing hETAR alone.

(7) Detection of an Antibody by Western Blot Analysis

Western blot analysis using the sera prepared by the above-mentioned step (6) as a primary antibody was carried out on the disrupted cell suspension containing MBP-hETAR fusion protein obtained in the above-mentioned step (5). PVDF membrane (Immobilon-P Millipore) was used for blotting, a biotin-labeled universal secondary antibody kit was used as a secondary antibody, and Konica Immunostain HRP-100 was used for detection. As a result, a band corresponding to the MBP-HETAR fusion protein was detected only in the serum of blood samplings after the $28^{th}$ day after immunization by pCI-hETAR-GroEL. Thereby, an antibody production against HETAR was induced by a fusion gene composed of an HETAR gene and a GroEL subunit gene.

EXAMPLE 2

In the present Example, gene immunization was compared with protein immunization.

(1) Gene Immunization by a Fusion Gene Composed of a Chaperonin Subunit Linkage Gene and a Human Endothelin A Receptor Gene A vector pCI-hETAR-GroEL was dissolved in saline so as to be at a concentration of 250 μg/mL, and whereby a composition for immunization was prepared. The composition for immunization was injected to femoral muscles of both legs of a BALB/c mouse aged 8 weeks (female), 0.12 mL to each, so as to immunize the mouse (day 0). Thereby, 30 μg of pCI-hETAR-GroEL was administered to each of the both legs, that is, 60 μg for one mouse per dose. Thereafter, immunization was repeatedly performed in a similar fashion on the $7^{th}$, the $21^{st}$, the $28^{th}$, and the $35^{th}$ days. Blood sampling was carried out on 0, the $7^{th}$, the $14^{th}$, the $21^{st}$, the $28^{th}$, the $35^{th}$, and $42^{nd}$ days, so as to give sera.

(2) Protein Immunization by a Fusion Protein Composed of a Chaperonin Subunit Linkage and Human Endothelin A Receptor (Control)

Oligonucleotides as shown in SEQ ID No. 11 and No. 12 were annealed, so as to give a double-stranded DNA. The double-stranded DNA was introduced into NcoI-HindIII sites of pTrc99A (Amersham Bioscience), so as to construct pTrc99AII. An SpeI site, an XbaI site, and a gene encoding FLAG-tag derived from the double-stranded DNA were introduced into pTrc99AII. Meanwhile, a DNA fragment containing a GroEL subunit gene (SEQ ID No. 10) was amplified by PCR using genomic DNA of *Escherichia coli* strain K12 as a template and oligonucleotides as shown in SEQ ID No. 13 and No. 14 as a primer set. Herein, an SpeI site and an XbaI site derived from the primers were introduced into the amplified DNA fragment respectively at its 5'-terminus and its 3'-terminus. This amplified DNA fragment was introduced into SpeI-XbaI sites of pTrc99AII, so as to construct pTrcGroEL.

Oligonucleotides as shown in SEQ ID No. 15 and No. 16 were annealed, so as to give a double-stranded DNA. The double-stranded DNA was introduced into DraIII-BamHI sites of pTrcGroEL, so as to construct pTrcSR1. That induced a mutation to a GroEL subunit gene on pTrcGroEL. The nucleotide sequence of the mutation-induced GroEL subunit gene (SR1 gene) is shown SEQ ID No. 24. pTrcSR1 was capable of expressing a modified GroEL subunit (SR1), which was given by substitution of the amino acid residues 452 of the GroEL subunit to a glutamic acid and of the amino acid residues 461, 463, and 464 to alanines.

A DNA fragment containing a SR1 gene was isolated by treatment of pTrcSR1 with SpeI and XbaI. The isolated DNA fragment was introduced into pTrcSR1 treated in advance with XbaI and BAP, so as to construct pTrcSR2, which contained a gene (SR2 gene) composed of two SRI genes linked to each other in one direction. Similarly, a DNA fragment containing a SR1 gene was introduced into pTrcSR2 treated in advance with XbaI and BAP, so as to construct pTrcSR3, which contained a gene (SR3 gene) composed of three SR1 genes linked to one another in one direction. Repetition of the similar operations constructed pTrcSR7, which contained a gene (SR7 gene) composed of seven SRI genes linked to one another in one direction. In other words, pTrcSR7 was capable of expressing a modified GroEL subunit 7-time linkage (SR7).

PCR using pCI-hETAR constructed in the step (3) in the Example 1 as a template and oligonucleotides as shown in SEQ ID No. 17 and No. 18 as a primer set, thereby amplifying a DNA fragment containing an hETAR gene (SEQ ID No. 3). Herein, an NheI site and an XhoI site derived from the primers were introduced into the amplified DNA fragment respectively at its 5'-terminus and its 3'-terminus. This amplified DNA fragment was introduced into pTrcSR7 treated in advance with NheI, XhoI, and BAP, so as to construct pTrcSR7-hETAR. pTrcSR7-hETAR was capable of expressing a fusion protein composed of SR7 and HETAR (hereinafter referred to as a "SR7-hETAR fusion protein"). Further, FLAG-tag was added to the C-terminus of the SR7-hETAR fusion protein.

pTrcSR7-hETAR was introduced into *E. coli* strain BL21 (DE3) to give a transformant. The transformant was rotary cultured at 23° C. and 110 rpm in 2×Y.T. medium containing carbenicillin (100 μg/mL) for 24 hours. After having cultured, cultured cells were recovered by centrifugation. The recovered cells were disrupted by sonication. The supernatant of the cell disruption was recovered by centrifugation. The supernatant was subjected to an immune precipitation reaction using anti-FLAG antibody-immobilized beads (Sigma). The obtained precipitated fraction was subjected to SDS-PAGE/CBB. As a result, a band was detected at a position adjacent to 470 kDa corresponding to a molecular weight of the SR7-hETAR fusion protein. Further, Western blot analysis using an anti-FLAG antibody was carried out, whereby this band reacted. These results showed that the SR7-hETAR fusion protein was expressed in a soluble fraction of E. coli.

The obtained supernatant was subjected to affinity chromatography using ANTI-FLAG Monoclonal antibody Agarose Affinity Gel (Sigma-Aldrich) and to hydrophobic chromatography using Butyl Sepharose FF (Amersham Bioscience), so that the SR7-hETAR fusion protein was purified.

Fifty μg of the purified SR7-hETAR fusion protein was subcutaneously injected to a BALB/c mouse aged 8 weeks (female), so as to immunize the mouse (day 0). Thereafter, as well as the gene immunization in the step (1) in the present Example 1, immunization was repeatedly performed on the $7^{th}$, the $21^{st}$, the $28^{th}$, and the $35^{th}$ days. Blood sampling 5 was carried out on 0, the $7^{th}$, the $14^{th}$, the $21^{st}$, the $28^{th}$, the $35^{th}$, and the $42^{nd}$ days, so as to give sera.

(3) Evaluation Results of ELISA

The cell disruption of E. coli containing MAL-HETAR (84 kDa) obtained in the step (5) in the Example 1 was subjected to Amylose Resin Column (New England Biolabs), whereby MAL-HETAR was bound to the resin. After having washed the resin, MAL-hETAR was eluted by maltose and recovered. The recovered MAL-HETAR was absorbed to a 96-well microtiter plate. ELISA was carried out using the 96-well microtiter plate, thereby evaluating anti-hETAR titer of each of the sera obtained by the gene immunization in the step (1) and the protein immunization in the step (2).

Herein, peroxidase-labeled anti-mouse IgG was used as a secondary antibody and TMB was used as a coloring substrate. Evaluation results by ELISA are shown in Table 1. In the Table 1, each numerical value is ELISA titer shown at dilution ratio of the serum. It showed that the higher its titer, the more an antibody was produced, that is, it revealed that humoral immunity was highly induced. The immunized mouse by protein immunization showed higher titer than the immunized mouse by gene immunization for a short period of time after the start of immunization until the $21^{st}$ day. However, titer of the mouse by gene immunization rapidly increased after this and showed titer having ten times higher than the mouse by protein immunization at the $42^{nd}$ day. Consequently, gene immunization induced higher humoral immunity than protein immunization.

TABLE

|  | (1) Gene immunization | (2) Protein immunization |
|---|---|---|
| Day 7 | <1/10 | 1/500 |
| Day 14 | 1/100 | 1/1,000 |
| Day 21 | 1/1,000 | 1/2,000 |
| Day 28 | 1/10,000 | 1/2,000 |
| Day 35 | 1/20,000 | 1/2,000 |
| Day 42 | 1/20,000 | 1/2,000 |

EXAMPLE 3

In the present Example, binding ability to active-type HETAR on the cell surface was evaluated on an anti-hETAR antibody in each serum obtained in the step (1) in the Example 2.

(1) Preparation of Human Endothelin A Receptor Expressing Cells and Endothelin B Receptor Expressing Cells PCR using pCI-hETAR-GroEL constructed in the step (3) in the Example 1 as a template and oligonucleotides as shown in SEQ ID No. 19 and No. 20 as a primer set was carried out to give a DNA fragment containing an HETAR gene. The obtained DNA fragment was introduced into NheI-XhoI sites of pCIneo (Promega), so as to construct pCIneo-hETAR. Meanwhile, PCR using a human placenta cDNA library (Takara Bio) as a template and oligonucleotides as shown in SEQ ID No. 21 and No. 22 as a primer set was carried out to give a DNA fragment containing a human endothelin B receptor (HETBR) gene (SEQ ID No. 23). The obtained DNA fragment was introduced into NheI-XhoI sites of pCIneo, so as to construct pCIneo-hETBR.

Thirty-seven point five μL of Lipofectamin solution, 625 μL of OPTI-MEMI medium, and 625 μL OPTI-MEMI medium containing 20 μg of pCIneo-hETAR were mixed to give a mixture, which was used to introduce pCIneo-hETAR into $2 \times 10^5$ COS7 cells (Dainippon Pharmaceutical). In similar procedures, pCIneo-hETBR was introduced into COS7 cells. As a control, only pCIneol was introduced into COS7 cells. Each of the COS7 cells, into which the gene was introduced, was cultured in Ham'sF12K+10% FBS medium (ICN) for 30 hours. Further, each of the COS7 cells were cultured for one day and night with a 96-well microtiter plate at an initial cell concentration of $2 \times 10^4/100$ μL. After having cultured, stimulation of each cell by ET-1 (Peptide Institute) in a range of concentration from $10^{-6}$ to $10^{-12}$ M resulted in transiently higher Ca concentration in the cells. The Ca concentration was evaluated using Ca signal analyzer (FLIPR; MD) and intracellular Ca stain kit (Ca3kit; MD) The result revealed that both of active-type HETAR and active-type HETBR were normally expressed on the cell membrane of COS7 cells.

(2) Evaluation Results of Binding Ability to Active-Type hETAR by Flow Cytometry The COS7 cells into which pCIneo-hETAR was introduced (hereinafter referred to as "hETAR gene-introduced cells"), the COS7 cells into which pCIneo-hETBR was introduced (hereinafter referred to as "hETBR gene-introduced cells"), and the COS7 cells into which pCIneol was introduced (control cells) were rinsed with PBS. The serum on the $35^{th}$ day after immunization, which was prepared in the Example 2, was diluted by 500 times and incubated with each of the cells. Further, after addition of a phycoerythrin-labeled anti-mouse IgG antibody (Beckman Coulter) as a secondary antibody, flow cytometric analysis using EPICS XL (Beckman coulter) was carried out on interaction between each of the cells and an anti-hETAR antibody in the serum. The results are shown in FIGS. 1, 2, and 3.

Figure 1B:
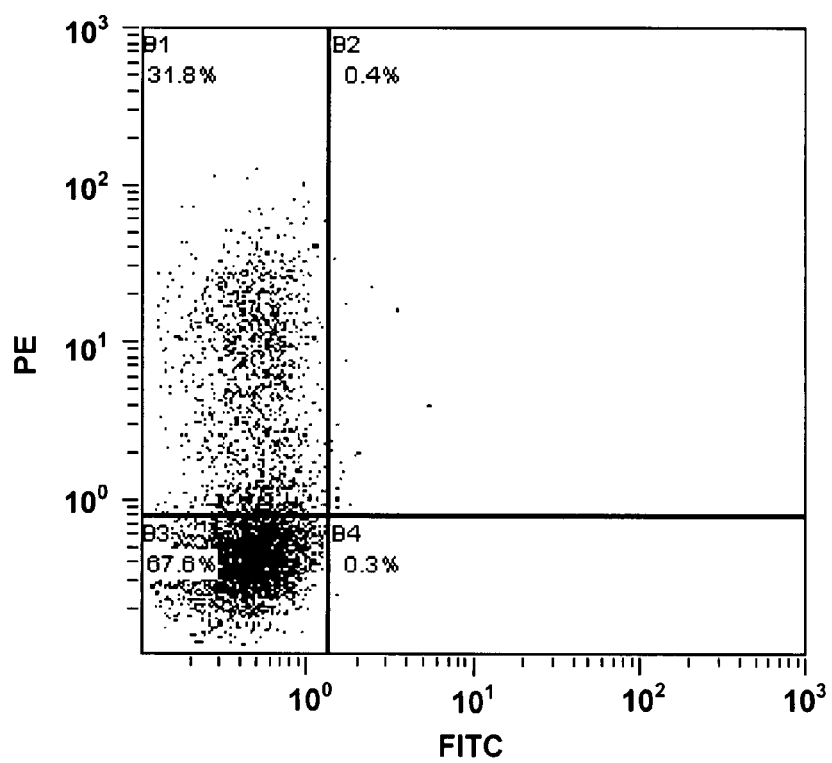
Figure 2A:
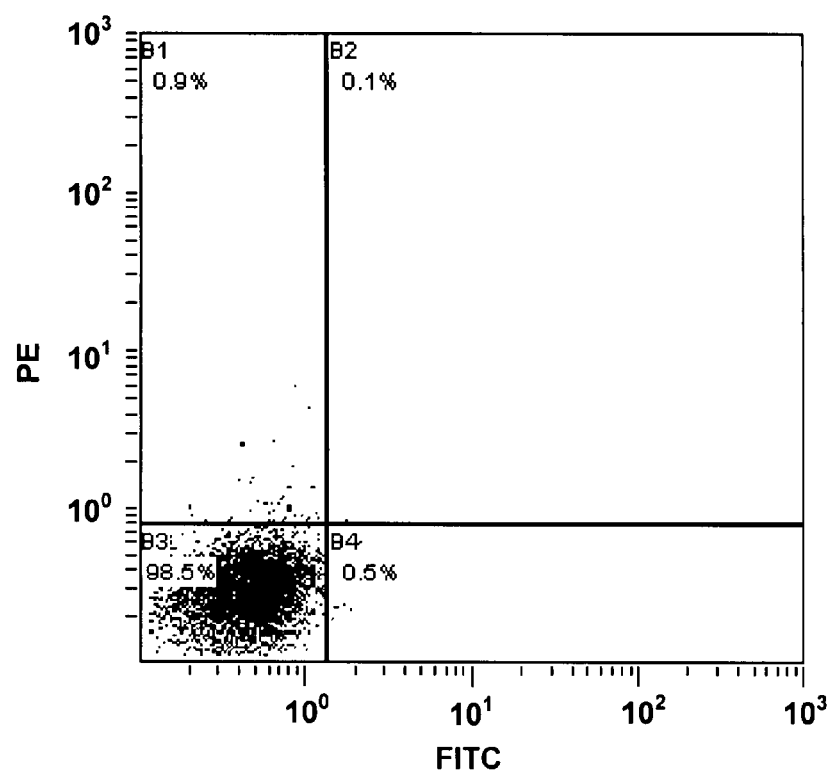
FIGS. 2A and 2B show analysis results of the interaction between hETBR gene-introduced cells and an anti-hETAR antibody in a serum in Example 3, FIG. 2A being a two-dimensional dot plot in the case of use of the serum before gene immunization (day 0), FIG. 1B being a two-dimensional dot plot in the case of use of the serum on the $35^{th}$ day after gene immunization.
Figure 2B:
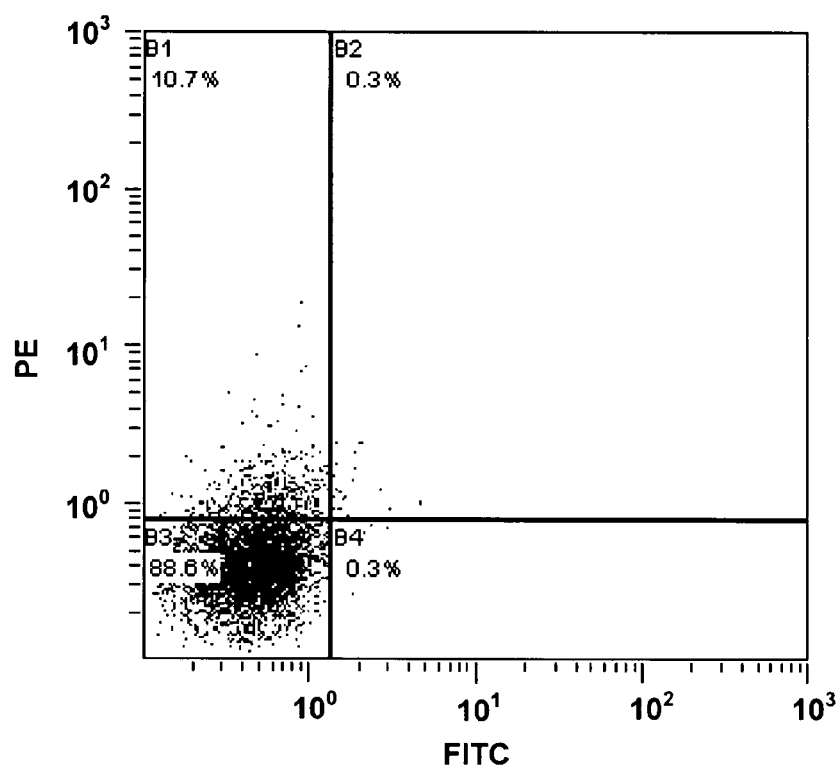
Figure 3A:
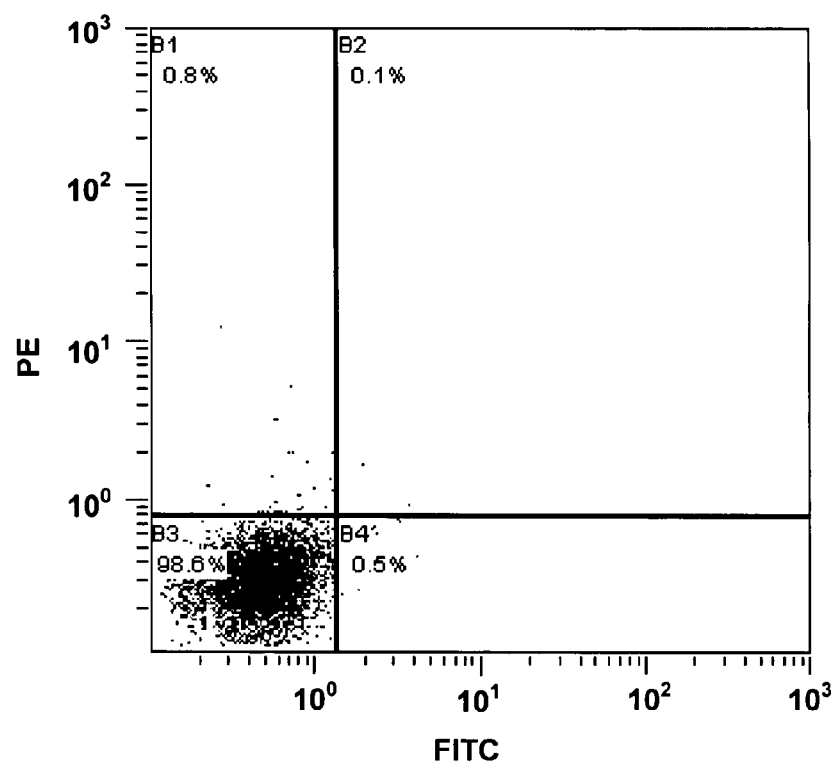
FIGS. 3A and 3B show analysis results of the interaction between control cells and an anti-hETAR antibody in a serum in Example 3, FIG. 3A being a two-dimensional dot plot in the case of use of the serum before gene immunization (day 0), FIG. 1B being a two-dimensional dot plot in the case of use of the serum on the 35$^{th}$ day after gene immunization.
Figure 3B:
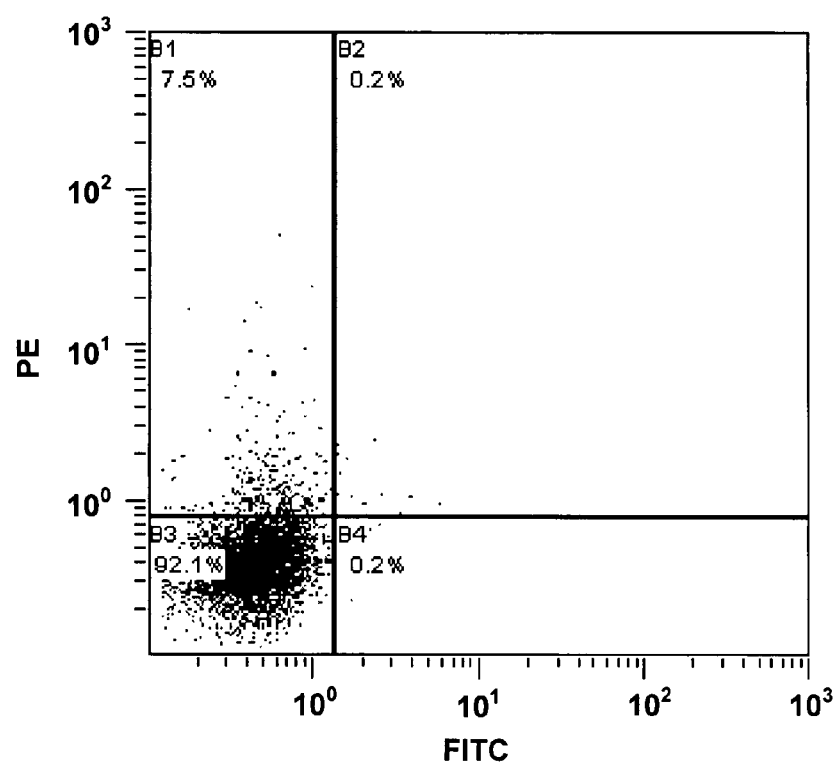

FIGS. 1A and 1B show analysis results of the interaction between HETAR gene-introduced cells and an anti-hETAR antibody in the serum, FIG. 1A being a two-dimensional dot plot in the case of use of the serum before gene immunization (day 0), FIG. 1B being a two-dimensional dot plot in the case of use of the serum on the $35^{th}$ day after gene immunization. FIGS. 2A and 2B show analysis results of the interaction between hETBR gene-introduced cells and an anti-hETAR antibody in the serum, FIG. 2A being a two-dimensional dot plot in the case of use of the serum before gene immunization (day 0), FIG. 1B being a two-dimensional dot plot in the case of use of the serum on the $35^{th}$ day after gene immunization. FIGS. 3A and 3B show analysis results of the interaction between the control cells and an anti-hETAR antibody in the serum, FIG. 3A being a two-dimensional dot plot in the case of use of the serum before gene immunization (day 0), FIG.

1B being a two-dimensional dot plot in the case of use of the serum on the 35$^{th}$ day after gene immunization. In FIGS. 1, 2, and 3, a vertical scale denotes fluorescence intensity derived from phycoerythrin (PE) and a horizontal scale denotes fluorescence intensity derived from fluorescein isothiocyanate (FITC). Dots in B1 (upper left) of four areas (B1 to B4) represent the cells bound to an anti-hETAR antibody in the serum. A value stated in each area denotes a percentage (%) of dots in the respective area.

As a result, in the case of the HETAR gene-introduced cells, dots were barely detected in B1 area in the serum before gene immunization (FIG. 1A), but many dots were detected in B1 area in the serum after gene immunization (FIG. 1B). That revealed that the anti-hETAR antibody in the serum after immunization was bound to the HETAR gene-introduced cells. In contrast, in the case of the HETBR gene-introduced cells, dots were barely detected in B1 area even in the serum after immunization (FIGS. 2A and 2B). That revealed that the anti-hETAR antibody in the serum after immunization was not bound to the HETBR gene-introduced cells. In the case of the control cells, dots were also barely detected in B1 area in the serum after gene immunization (FIGS. 3A and 3B). That revealed that the anti-hETAR antibody in the serum after immunization was not bound to the control cells. These results showed that gene immunization induced production of an antibody specifically recognizing an extracellular domain of active-type HETAR.

The invention claimed is:

1. A method for producing an antibody, comprising the steps of:
   immunizing an animal by administering a fusion gene to an animal, the fusion gene being composed of a gene encoding the full-length or a part of an antigen protein, the antigen protein being one selected from the group consisting of a G protein-coupled receptor, an ion channel-linked receptor, and a tyrosine kinase-type receptor, and a gene encoding one selected from a chaperonin subunit and a chaperonin subunit linkage linked thereto, so as to express the fusion gene in the animal to induce a humoral immune response to the antigen protein, so that an antibody against the antigen protein is produced in the animal; and
   obtaining the antibody from the animal by isolation from serum.

2. The method as defined in claim 1,
   wherein the one selected from the chaperonin subunit and the chaperonin subunit linkage is derived from *Escherichia coli*.

3. The method as defined in claim 1,
   wherein the fusion gene is integrated into an expression vector and expressed under control of a promoter on the expression vector.

4. The method as defined in claim 3,
   wherein the promoter is one selected from the group consisting of a CMV promoter, an AML promoter, an SV40 promoter, an SRα promoter, and an EF-1α promoter.

5. The method as defined in claim 3,
   wherein the expression vector contains a CpG motif.

6. The method as defined in claim 1,
   wherein the animal is one selected from a mammal and a bird.

7. The method as defined in claim 6,
   wherein the mammal is one selected from the group consisting of a mouse, a rat, a rabbit, a bovine, a horse, a dog, a cat, a goat, a sheep, and a pig.

8. The method as defined in claim 6,
   wherein the bird is one selected from the group consisting of a chicken, a duck, and a turkey.

9. The method as defined in claim 1,
   wherein the one selected from the chaperonin subunit and the chaperonin subunit linkage is derived from bacteria.

10. A method for producing a hybridoma, comprising the steps of:
    immunizing an animal by administering a fusion gene to an animal, the fusion gene being composed of a gene encoding the full-length or a part of an antigen protein, the antigen protein being one selected from the group consisting of a G protein-coupled receptor, an ion channel-linked receptor, and a tyrosine kinase-type receptor, and a gene encoding one selected from a chaperonin subunit and a chaperonin subunit linkage linked thereto, so as to express the fusion gene in the animal to induce a humoral immune response to the antigen protein;
    obtaining an immunocyte from the animal; and
    fusing the immunocyte and a myeloma,
    so as to prepare a hybridoma producing an antibody against the antigen protein.

11. A method for producing a monoclonal antibody, comprising the steps of:
    culturing the hybridoma produced by the method as defined in claim 10; and
    obtaining a monoclonal antibody against the antigen protein from the culture of the hybridoma.

12. The method as defined in claim 10,
    wherein the one selected from the chaperonin subunit and the chaperonin subunit linkage is derived from bacteria.

13. The method as defined in claim 10,
    wherein the one selected from the chaperonin subunit and the chaperonin subunit linkage is derived from *Escherichia coli*.

14. The method as defined in claim 10,
    wherein the fusion gene is integrated into an expression vector and expressed under control of a promoter on the expression vector.

15. The method as defined in claim 14,
    wherein the promoter is one selected from the group consisting of a CMV promoter, an AML promoter, an SV40 promoter, an SRα promoter, and an EF-1α promoter.

16. The method as defined in claim 14,
    wherein the expression vector contains a CpG motif.

17. The method as defined in claim 10,
wherein the animal is one selected from a mammal and a bird.

18. The method as defined in claim 17,
wherein the mammal is one selected from the group consisting of a mouse, a rat, a rabbit, a bovine, a horse, a dog, a cat, a goat, a sheep, and a pig.

19. The method as defined in claim 17,
wherein the bird is one selected from the group consisting of a chicken, a duck and a turkey.

20. A method for producing a monoclonal antibody, comprising the steps of:
culturing the hybridoma produced by the method as defined in claim 12; and
obtaining a monoclonal antibody against the antigen protein from the culture of the hybridoma.

21. A method for producing a monoclonal antibody, comprising the steps of:
culturing the hybridoma produced by the method as defined in claim 13; and
obtaining a monoclonal antibody against the antigen protein from the culture of the hybridoma.

22. A method for producing a monoclonal antibody, comprising the steps of:
culturing the hybridoma produced by the method as defined in claim 14; and
obtaining a monoclonal antibody against the antigen protein from the culture of the hybridoma.

23. A method for producing a monoclonal antibody, comprising the steps of:
culturing the hybridoma produced by the method as defined in claim 15; and
obtaining a monoclonal antibody against the antigen protein from the culture of the hybridoma.

24. A method for producing a monoclonal antibody, comprising the steps of:
culturing the hybridoma produced by the method as defined in claim 16; and
obtaining a monoclonal antibody against the antigen protein from the culture of the hybridoma.

25. A method for producing a monoclonal antibody, comprising the steps of:
culturing the hybridoma produced by the method as defined in claim 17; and
obtaining a monoclonal antibody against the antigen protein from the culture of the hybridoma.

26. A method for producing a monoclonal antibody, comprising the steps of:
culturing the hybridoma produced by the method as defined in claim 18; and
obtaining a monoclonal antibody against the antigen protein from the culture of the hybridoma.

27. A method for producing a monoclonal antibody, comprising the steps of:
culturing the hybridoma produced by the method as defined in claim 19; and
obtaining a monoclonal antibody against the antigen protein from the culture of the hybridoma.

28. A method for producing a monoclonal antibody, comprising the steps of:
immunizing an animal by administering a fusion gene to an animal, the fusion gene being composed of a gene encoding the full-length or a part of an antigen protein, the antigen protein being one selected from the group consisting of a G protein-coupled receptor, an ion channel-linked receptor, and a tyrosine kinase-type receptor, and a gene encoding one selected from a chaperonin subunit and a chaperonin subunit linkage linked thereto, so as to express the fusion gene in the animal to induce a humoral immune response to the antigen protein;
preparing mRNA against an antibody from the animal; and
preparing cDNA from the mRNA used as a template,
so that a monoclonal antibody against the antigen protein is prepared by a phage display method using the cDNA.

\* \* \* \* \*